(12) United States Patent
Uhlhorn et al.

(10) Patent No.: US 8,425,037 B2
(45) Date of Patent: Apr. 23, 2013

(54) INTRAOPERATIVE IMAGING SYSTEM AND APPARATUS

(75) Inventors: Stephen Uhlhorn, Palm Beach Gardens, FL (US); Marco Ruggeri, Miami, FL (US); Fabrice Manns, Palmetto Bay, FL (US); Jean-Marie Arthur Parel, Miami Shores, FL (US)

(73) Assignee: Adventus Technologies, Inc., Irvine, CA (US)

( * ) Notice: Subject to any disclaimer, the term of this patent is extended or adjusted under 35 U.S.C. 154(b) by 18 days.

(21) Appl. No.: 13/194,067

(22) Filed: Jul. 29, 2011

(65) Prior Publication Data

US 2012/0026462 A1   Feb. 2, 2012

Related U.S. Application Data

(60) Provisional application No. 61/369,269, filed on Jul. 30, 2010.

(51) Int. Cl.
*A61B 3/14* (2006.01)
*A61B 3/00* (2006.01)

(52) U.S. Cl.
USPC .......................................... 351/206; 351/246

(58) Field of Classification Search ........... 351/200–246
See application file for complete search history.

(56) References Cited

U.S. PATENT DOCUMENTS

| | | | |
|---|---|---|---|
| 5,493,109 A | 2/1996 | Wei et al. | |
| 6,004,314 A | 12/1999 | Wei et al. | |
| 6,775,007 B2 * | 8/2004 | Izatt et al. | 356/497 |
| 7,697,145 B2 * | 4/2010 | Izatt | 356/497 |
| 7,699,468 B2 | 4/2010 | Gaida | |
| 7,719,692 B2 | 5/2010 | Izatt et al. | |
| 7,841,719 B2 * | 11/2010 | Podoleanu | 351/212 |
| 2009/0257065 A1 | 10/2009 | Hauger et al. | |
| 2011/0102802 A1 | 5/2011 | Izatt et al. | |
| 2011/0267340 A1 * | 11/2011 | Kraus et al. | 345/419 |

OTHER PUBLICATIONS

Zvyagin, Andrei V., et al., "Delay and Dispersion Characteristics of a Frequency-Domain Optical Delay Line for Scanning Interferometry", Feb. 2003, vol. 20, No. 2, J. Opt. Soc. Am. A.

* cited by examiner

*Primary Examiner* — Mohammed Hasan
(74) *Attorney, Agent, or Firm* — Smith Moore Leatherwood LLP

(57) ABSTRACT

Systems, methods and apparatuses for intraocular imaging system are disclosed comprising an optical coherence tomography (OCT) system. The OCT system has an imaging range that may enable substantial portions of an eye to be imaged. The OCT system may be coupled to an operation microscope, such that, for example, a surgeon can visualize ocular structures like the human crystalline lens and other ocular structures such as the cornea and/or vitreous while surgical instruments are in the field of view.

24 Claims, 9 Drawing Sheets

INTRAOPERATIVE IMAGING SYSTEM AND APPARATUS

RELATED APPLICATION

This application is related to and claims priority from U.S. patent application 61/369,269 filed Jul. 30, 2010, the entire content of which is incorporated herein by reference.

FIELD

The present invention is directed generally to the field of methods and apparatuses for imaging internal ocular components (referred to herein as intraocular imaging methods and systems).

BACKGROUND

Typical ocular surgery, such as, for example, cataract surgery, is routinely performed without the aid of specialized imaging equipment or procedures beyond an operation microscope. However, in the case of a complex or otherwise difficult ocular surgery, including but not limited to lens refilling following capsulorhexis procedures, a surgeon would benefit greatly from the aid of a real time, cross-sectional view. For example, during cataract or other ocular surgical procedures, such a real time, cross-sectional view of the crystalline lens would greatly enhance the surgeon's ability to complete the procedure.

Optical coherence tomography (OCT) is a noninvasive imaging technique that measures backscattered light as a function of depth to provide subsurface imaging with high spatial resolution in three dimensions with no contact needed between the probe and the tissue. An OCT system uses an interferometer in which light from a broadband source is split between illuminating the sample of interest and a reference path. The interference pattern of light reflected or backscattered from the sample and light from the reference delay is used to produce an image of the sample.

Types of OCT include time domain OCT (TD-OCT) and Fourier domain OCT (FD-OCT). In TD-OCT the interference pattern is obtained by scanning the reference path delay and detecting the resulting interferogram pattern as a function of the delay. In FD-OCT, sample light is mixed with reference light at a fixed group delay as a function of optical wave number to obtain the interferogram pattern. FD-OCT has been shown to result in images with an improved signal to noise ratio (SNR). Two types of FD-OCT are typically used: spectral domain OCT (SD-OCT) and swept-source OCT (SS-OCT). SDOCT uses a broadband light source and a dispersive spectrometer in the detector arm. SS-OCT time-encodes the wave number by rapidly tuning a narrowband source through a broad optical bandwidth.

While OCT technology would appear to be beneficial in the context of cataract surgery, it has to date been used mostly for diagnostic purposes. One of the limitations of presently known OCT technology that prevents its use for surgery is the limited scan depth that is obtainable.

OCT systems are described in U.S. Patent Publication Number US 2009/0257065, and U.S. Pat. Nos. 5,493,109; 6,004,314; 7,699,468, all of which are incorporated by reference herein, as if made a part of this specification.

Embodiments of an OCT system with a reference arm optical switch are described in U.S. Patent Application Publication US 2011/0102802 A1, also incorporated by reference herein, as if made a part of this specification. This patent publication describes using the switch to image two distinct structures independently.

SUMMARY

Embodiments of the present invention generally relates to ocular imaging systems for imaging over a depth range. In various embodiments, the ocular imaging system provides the imaging over the depth range by combining scans at two overlapping image ranges, by removing artifacts, compensating for dispersion, and positioning the depth ranges having regard to minimising mirror-image artifacts.

According to embodiments of the present invention, an intraocular imaging method is disclosed that includes receiving, with an optical coherence tomography system, image data of an ocular system at a first image depth range and a second image depth range, forming a first A-scan from the image data at the first image depth range, forming a second A-scan from the image data at the second image depth range, the second range overlapping the first image depth range across an overlap region, cropping said first and second A-scans at a location in the overlap region, and producing a composite image by combining the cropped first and second A-scans.

In a further embodiment, the present invention is directed to an intraocular imaging method includes receiving, with an optical coherence tomography system, raw image data of an ocular system at an image depth range and forming an A-scan from the raw image data in a process that comprises removing artifacts from the raw data. The artifacts may be removed by performing a background subtraction to provide cleaned raw data. The background subtraction may include subtracting an array of values representing autocorrelation artifacts and fixed pattern noise. The method may further include, before the background subtraction, forming a plurality of A-scans and forming the array of values by averaging the plurality of A-scans.

In a further embodiment, the present invention is directed to an intraocular imaging method includes receiving imaging data in the form of wavelength data and forming an A-scan from the wavelength data by converting the wavelength data into non-linear frequency domain data, resampling the frequency array to provide linearized data and processing the linearized data to provide the A-scan. The processing may include performing a Fourier transform on the linearized data to provide an intensity profile and a complex result, determining an absolute value of the complex result to provide magnitude data, and determining a logarithm of the magnitude data to provide a compressed dynamic range.

According to the present invention, in further embodiments of the imaging methods, the method includes forming a first B-scan comprising a plurality of said A-scans at a first image depth range, forming a second B-scan comprising a plurality of A-scans at the second image depth range and producing a composite image combining the first B-scan and the second B-scan. Further B-scans may be combined to form the composite image. A further B-scan may overlap with the first or second B-scans or may be provided at distinct non-overlapping depth range.

Intraocular imaging methods, according to embodiments of the present invention, further comprise receiving image data using an optical coherence tomography system that includes an interferometer including a reference arm and a sample arm and providing a selected amount of dispersion compensating material in the reference arm.

Further intraocular imaging methods, according to embodiments of the present invention, further comprise receiving imaging data at a first image depth range and at a second image depth range, different from the first image depth range, wherein the location of the first and second image depth ranges is selected so that image data includes substantially no mirror-image artifacts. When the ocular system includes a cornea and a crystalline lens, the first image depth range may be selected so that a zero delay location of an optical coherence tomography system is located anterior to the cornea and the second image depth range is selected so that the zero delay location of the optical coherence tomography is located posterior to the crystalline lens. In this way an image of the anterior segment of an eye may be formed.

Still further intraocular imaging methods, according to embodiments of the present invention, further comprise performing optical coherence tomography system through an objective lens configured to provide a focal plane and imaging at imaging depths, so that focal plane is located at a mid-point between a zero delay location at the imaging depths or in a region of overlap of the imaging depths. The optical coherence tomography system may include a first and a second lateral scanner for providing a B-scan and the optical coherence tomography system may be configured to have a back focal plane located between the first and the second lateral scanner.

The intraocular imaging methods described above may be implemented individually, or in any combination, each such combination being hereby incorporated herein as if individually set forth. The methods may also be varied or supplemented with other steps as described herein.

According to one embodiment of the present invention, an intraocular imaging system is disclosed, comprising a spectrometer, an interferometer comprising a sample arm and a reference arm, and an image processor. The interferometer is configured to comprise a plurality of optical paths of different path lengths along the reference arm and switch between the optical paths, the optical paths causing the imaging system to image at different and overlapping imaging ranges. The intraocular system is arranged to operate said optical scanner and interferometer to provide the image processor B-scan data at said path lengths and wherein the image processor is arranged to combine the B-scan data to form a composite image extending over an imaging range longer than the imaging ranges formed by the individual path lengths.

According to further embodiments of the present invention, an objective lens of the intraocular imaging system is configured to provide a focal plane at a location in the overlap of the overlapping imaging ranges. When the image processor is arranged to combine B-scan data, it may be arranged to do so by cropping the B-scan data at said path lengths at or around a location corresponding to the location of the focal plane of the objective lens. The intraocular imaging system may include lateral scanners for controlling a position of the imaging ranges to enable B-scans to be formed and a back focal plane of an objective lens of the imaging system may be located between the lateral scanners.

According to further embodiments, an intraocular imaging system of the present invention comprises a spectrometer, an interferometer comprising a sample arm and a reference arm, and an image processor. In the reference arm is a movable dispersion compensating material that is configured so that movement of the material varies the amount of said dispersion compensating material in the optical path of the reference arm.

Still further, according to embodiments of the present invention, an intraocular imaging system comprises a spectrometer, an interferometer comprising a sample arm and a reference arm, and an image processor. The interferometer includes a sensor that includes pixels distributed across individual pixel locations. The image processor processes image data from the sensor using a map of the individual pixel locations to their corresponding wavelength. The map is configured to calibrate for non-linear distribution of the wavelengths across the pixel locations.

According to further embodiments, an intraocular imaging system of the present invention may be formed using any combination of the features described above, each such combination being hereby incorporated herein as if individually set forth. The imaging systems may also be varied or supplemented with other integers described herein.

BRIEF DESCRIPTION OF THE DRAWINGS

The foregoing and other features and embodiments of the present invention may be better understood by referring to the description of preferred embodiments and claims which follow, taken together with the accompanying drawings wherein:

In the drawings, like reference numerals refer to equivalent features.

DETAILED DESCRIPTION

Figure 1:
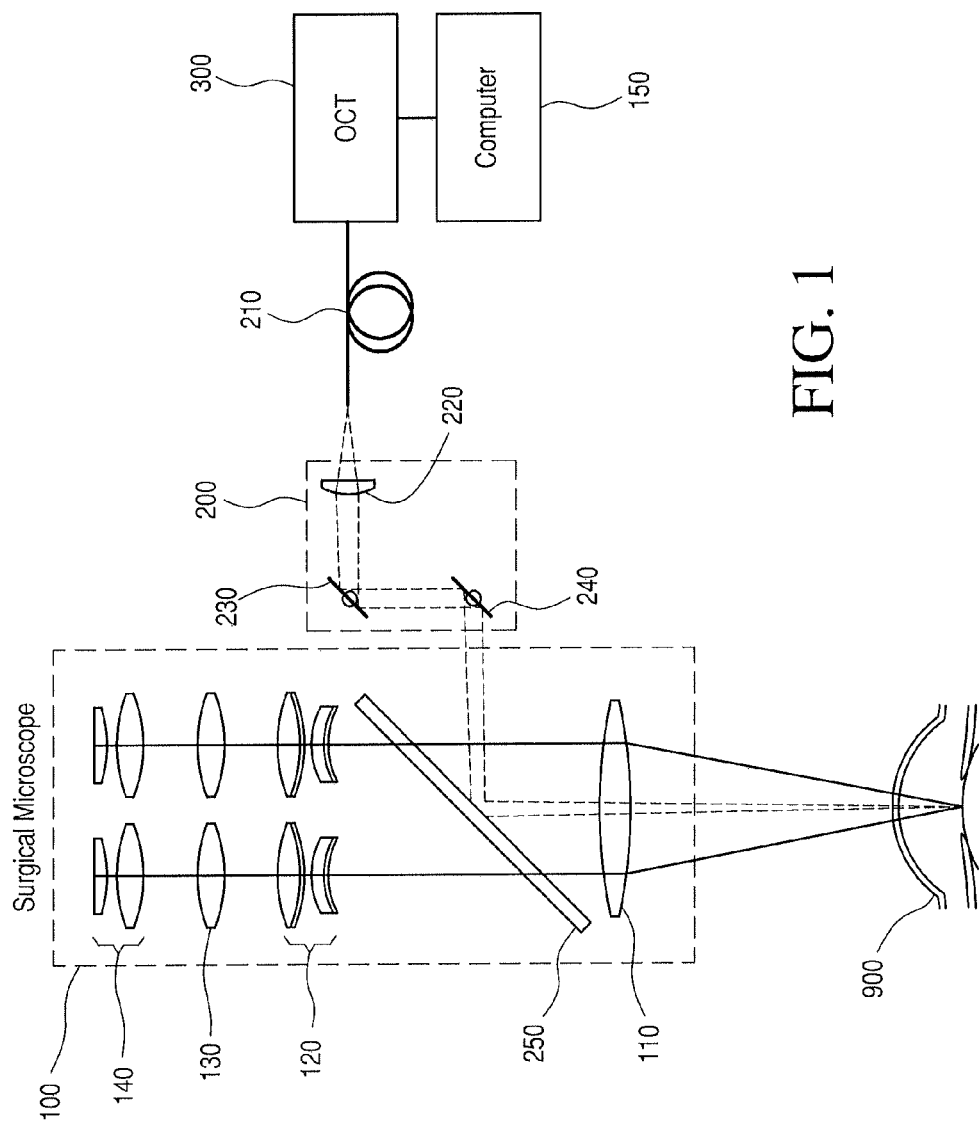
FIG. 1 is a schematic diagram of one embodiment of a combined ophthalmic surgical microscope and optical coherence tomography (OCT) apparatus.

One embodiment of an intraocular imaging system comprises at least two main components: 1) an optical coherence tomography (OCT) system capable of generating a cross-sectional view of at least substantially the entire portion of the crystalline lens not hidden by the iris, and 2) a delivery system capable of interfacing the OCT system to an operation microscope, such that, for example, a surgeon can visualize the crystalline lens while surgical instruments are in the field of view. The following description is provided primarily with reference to intraocular imaging systems of this form, which will have other applications in addition to visualization of a crystalline lens.

In other embodiments the intraocular imaging system is integrated in a slit-lamp biomicroscope or a handheld device, such as a handheld microscope and in some embodiments the intraocular imaging system may stand alone.

As implemented in embodiments of the present invention, the novel OCT system provides a substantially real-time, cross-sectional image enabling the surgeon to visualize, for example, a crystalline lens while performing surgery. This is accomplished by providing an OCT video image of the lens in at least one of the operation microscope oculars, to an external display, or both. The human crystalline lens is, on average, approximately 5 mm in maximum physical thickness. For the scan depth (axial) to be large enough to image the entire crystalline lens, this requires that the scan depth of the OCT system be greater than the optical thickness (7-8 mm). The long-range depth scanning requirement can be satisfied using a number of techniques, including, for example, 1) a high spectral-resolution imaging spectrometer designed to achieve the required depth range, 2) an optical switching method implemented in the reference arm of the interferometer, or 3) both.

One component of the OCT system that contributes to achieving the extended depth range is the high spectral-resolution imaging spectrometer. The spectrometer described herein preferably employs a single line camera and a single transmission grating to achieve long axial range (approximately 10 mm in air, approximately 7-8 mm in tissue, including tissue that may be up to 99% water when used with FD-OCT with a fixed group delay). The design parameters define the spectral resolution of the spectrometer, which is related to the detectable depth range of a SD-OCT through the following formula (Eq. 1):

$$\Delta z = \frac{1}{4n} \frac{(\lambda_0)^2}{\delta \lambda} \quad \text{Eq. (1)}$$

where n is the refractive index of the sample examined with the OCT system and $\lambda_0$ is the central wavelength of the light source used in the OCT system.

According to preferred embodiments of the present invention, the optical scanning system is preferably fixed to the operation microscope since the surgeon's hands are often occupied with surgical instruments. This can be accomplished by two methods: 1) an external fixation and delivery of the OCT beam, or 2) an internal OCT beam delivery system that uses the operation microscope's primary objective to focus the OCT beam on the patient. For the external delivery method, the transverse optical scanners, scan lens, and optionally a dichroic beam splitter are positioned and mounted on the operation microscope, preferably positioned beneath the microscope objectives.

According to embodiments of the present invention, combining the two components of a long depth range OCT system with a delivery system integrated with the operation microscope produces a system that allows a surgeon to visualize the lens in cross-section. This is advantageous in a lens-refilling procedure, for example after capsulorhexis, so that the surgeon has visual feedback during refilling regarding the effect of the amount of material that is being injected into the lens capsule. Such a system would also be useful for femtosecond crystalline lens and cataract surgery. Furthermore, by employing a high-speed line scan camera utilizing either CCD or CMOS technology in the imaging spectrometer, fast acquisition rates are possible. The high acquisition rates enable either up to or higher than video-rate 2D cross-sectional imaging or recording of entire 3D volumes, for example 3D images of substantially entire ocular components such as, for example, lenses and components for which 2D cross-sectional imaging is possible, or selected portions thereof as desired. From either data source, quantitative analysis is possible to perform biometric measurements of the lens both before and after surgical procedures, including, for example, thickness, surface curvatures, diameter, etc.

Embodiments of the spectrometer described herein may have free-space scan depths of approximately 10 mm, or approximately 7-8 mm in tissue. This depth range is required for in vivo imaging of the crystalline lens during surgery, where tissue manipulation during surgery would otherwise move the object out of the imaging frame. When such a spectrometer is combined with the optical switching methods described herein, the free-space scan depth may be extended to be greater than 9 mm in tissue, for example to 12.7 mm. This depth range is sufficient to image the whole anterior segment of the human eye, from the anterior surface of the cornea to the posterior surface of the crystalline lens. The depth range is required for lens-refilling surgical procedures, where the location and orientation of the lens capsular bag with respect to the other anterior segment structures, such as the cornea, would greatly benefit the surgeon.

The imaging system described herein can also be used for quantitative analyses of tissue shape, including the radii of curvature, as well as thickness of both the cornea and lens, even during surgery. Such ability would have utility during lens refilling procedures as a practitioner would be able to "view" the procedure and reduce the risk of under- or over-filling the lens capsular bag. Other surgeries in which embodiments of the intraocular imaging system may have utility include, but are not limited to, DALK, DSEAK and KPro procedures as well as cataract surgery with IOL implantation.

FIG. 1 shows a schematic diagram of an embodiment of an intraocular imaging system, which comprises operation microscope 100 and optical coherence tomography (OCT) system 300.

The operation microscope 100 consists of objective lens 110, which has a long working distance (100-200 mm) for focusing on a patient's eye 900 during a surgical procedure such as femtosecond laser surgery. Light from the focal plane is collected and collimated by objective lens 110 and directed to magnifier 120. Magnifier 120 is a beam expander with multiple lens sets, or a zoom lens system to provide multiple magnifications to the observer. The collimated beam is focused by relay lens 130 to form an intermediate image of the object which is located at object plane of eyepieces 140. Eyepieces 140 then provide collimated light output, forming a magnified image of the patient's eye 900.

The operation microscope 100 described in FIG. 1 is understood to be in a fundamental form. It is to be understood by those skilled in the art that other elements may be included in the optical path to add greater functionality. Other embodiments of the ocular imaging system include integrating it with a slit-lamp biomicroscope or with a stand-alone hand-held delivery system.

As shown in FIG. 1, a primary objective lens of the surgical microscope (not shown) has been removed and has been replaced with an assembly consisting of beamcombiner 250 and the objective lens 110 with focal length chosen to optimize the beam delivery characteristics of the OCT system, to be described below.

Figure 2:
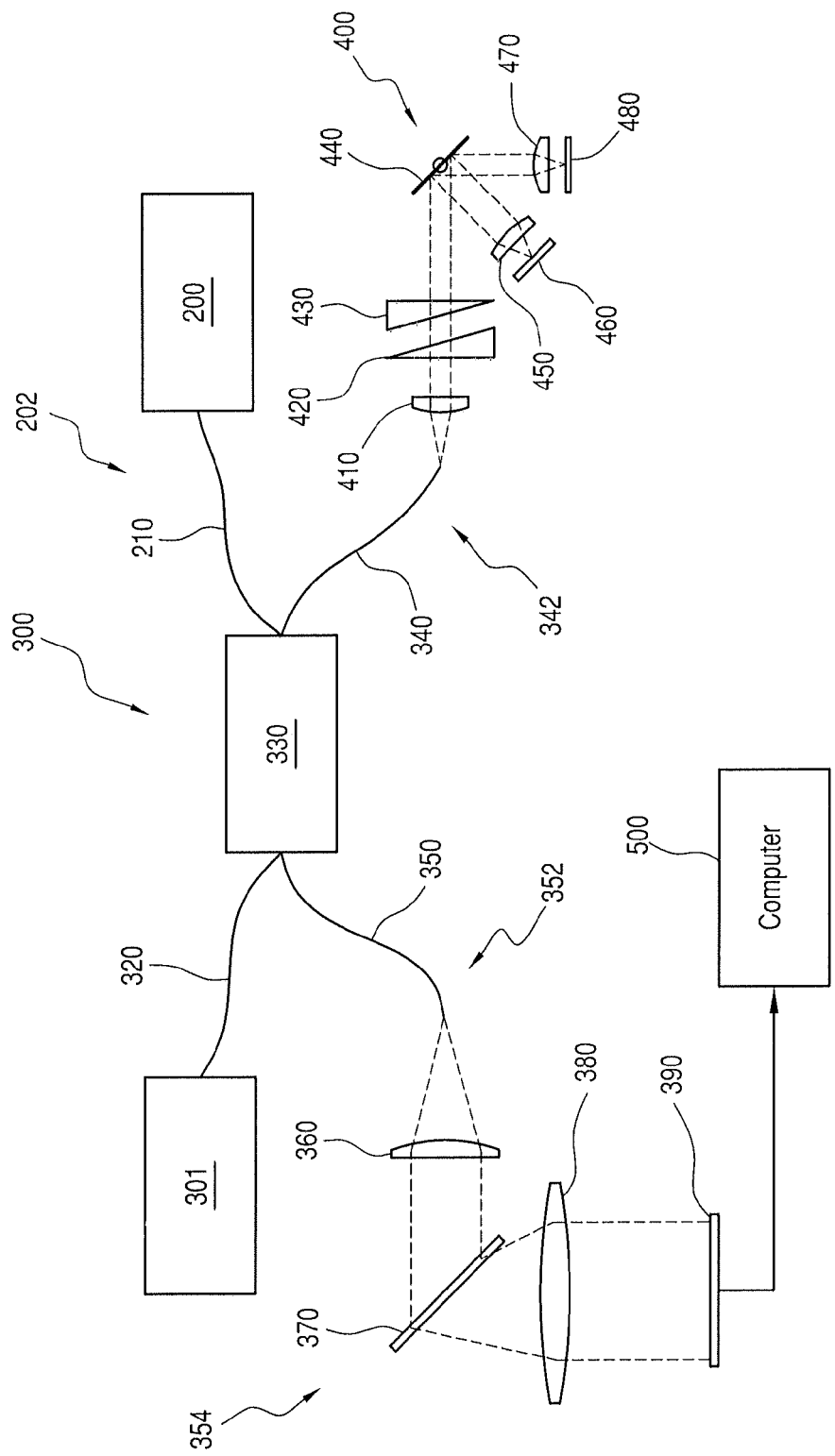
FIG. 2 is a schematic diagram of the OCT apparatus shown in FIG. 1, comprising a light source, fiber optic interferometer, and detection unit including an imaging spectrometer, and reference arm incorporating fast scanning optical switch.

The optical output of OCT system 300 is delivered to the surgical microscope 100 via transverse scanning unit 200 in the interferometer's sample arm 202 (shown in FIG. 2). The output of optical fiber 210 is collimated by lens 220 and directed to optical scanners 230 and 240. Optical scanners 230 and 240 are optical mirrors typically mounted on pivoting galvanometers whose position is controlled by computer 150. The collimated OCT beam is delivered to the surgical microscope and is combined with the optical path by beam-combiner 250. Beam-combiner 250 is a dichroic filter, such as a hot mirror that reflects wavelengths higher than about 750 nm and transmits wavelengths that are lower than about 750 nm. The OCT beam is focused by surgical microscope objective lens 110. Objective lens 110 also focuses the collimated light from the operation microscope, ensuring that the focal plane of operation microscope 100 and the focal plane of the OCT beam are the same. The location of objective lens 110 is such that the back focal plane (BFP) is located at the midpoint between optical scanners 230 and 240. This ensures that the OCT beam is scanned across objective lens 110 in a manner to be described in detail below. The selection of the focal length is described below with reference to Equation 9.

FIG. 2 shows a schematic diagram of a SD-OCT system 300 with an optical switch 400 in the reference arm 342, transverse scanning unit 200 that interfaces to the surgical microscope 100, and high-resolution imaging spectrometer 354 in the detection arm 352.

The OCT system employs a low-coherence light source 310, which may be a light emitting diode (LED), superluminescent diode (SLD), femtosecond laser source or other white light source, having a center wavelength in the near infrared (NIR) spectral region, centered near 800-850 nm. In other embodiments, different wavelength regions are possible, including, but not limited to the 900, 1060, and 1300 nm spectral bands. The radiation emitted by source 310 is coupled into input optical fiber 320 of single mode fiber optic coupler 330. In the embodiment shown the interferometer includes a 2×2 fiber optic coupler 330. Light coupled into the input optical fiber 320 is split into reference arm optical fiber 340 and optical fiber 210. The output of reference arm optical fiber 340 is reflected by fast-scanning optical switch 400 described below and coupled back to the reference arm optical fiber 340. The output of optical fiber 210 is directed to transverse scanning unit 200 described above and interfaces to surgical microscope at beamcombiner 250 shown in FIG. 1. Objective lens 110 focuses the optical output of transverse scanning unit 200. The radiation that is backscattered from patient's eye 900 is collected by the optical fiber 210 and combined with the radiation collected by optical fiber 340 returning from fast-scanning optical switch 400. Fiber optic coupler 330 combines the reflected light and a portion of the optical output, which includes the image information for detection is directed to the detection arm optical fiber 350.

Referring to FIG. 2, the output of the optical fiber 350 is collimated by lens 360 and directed to diffraction grating 370.

Light dispersed by diffraction grating 370 is collected by objective lens 380 and the individual wavelength components of light source 310 are focused onto a linear array detector 390 which may be a CCD or CMOS sensor. The digitized electronic output of detector 390 is collected by a dedicated capture card (not shown) and sent to computer 500 for processing and display. The line density of diffraction grating 370 and the focal length and aperture of imagine lens 380 are selected to spread adequately the bandwidth of light source 310 over the sensitive length of sensor 390.

Interference between light backscattered by the delivery arm object and the light reflected by the reference arm 342 fast scanning optical switch 400 occurs only when the optical path length difference between the reference and sample arms of the interferometer is within the coherence length of light source 310.

Under this condition, spectral interference fringes at different spatial frequencies illuminate sensor 390. The spatial frequency of the interference fringes encodes the axial position of scatterers in the sample. Increasing optical frequency corresponds to larger optical path length differences, that is, longer axial lengths, or deeper sample depths.

In the specific OCT system embodiment shown in FIG. 2, the imaging spectrometer 354 in the detection arm 352 is designed to have an extended depth range, according to the criteria described above. The specific design parameters of the spectrometer 354 that are required to achieve the extended depth range are dependent on the specific light source used in the OCT system.

In one embodiment, light source 310 is a superluminescent diode (SLD) with center wavelength $\lambda_0$=836 nm, full-width, half-maximum (FWHM) bandwidth of $\Delta\lambda_{FWHM}$=50 nm, and full bandwidth at the 1% output power level of $\Delta\lambda_1$%=68 nm, with a spectral range from $\lambda_1$=802 nm to $\lambda_2$=870 nm. It is to be understood that while the design details of the extended depth spectrometer are matched to the specifications of the light source employed, other light sources can be used to achieve the required depth range.

Figure 3:
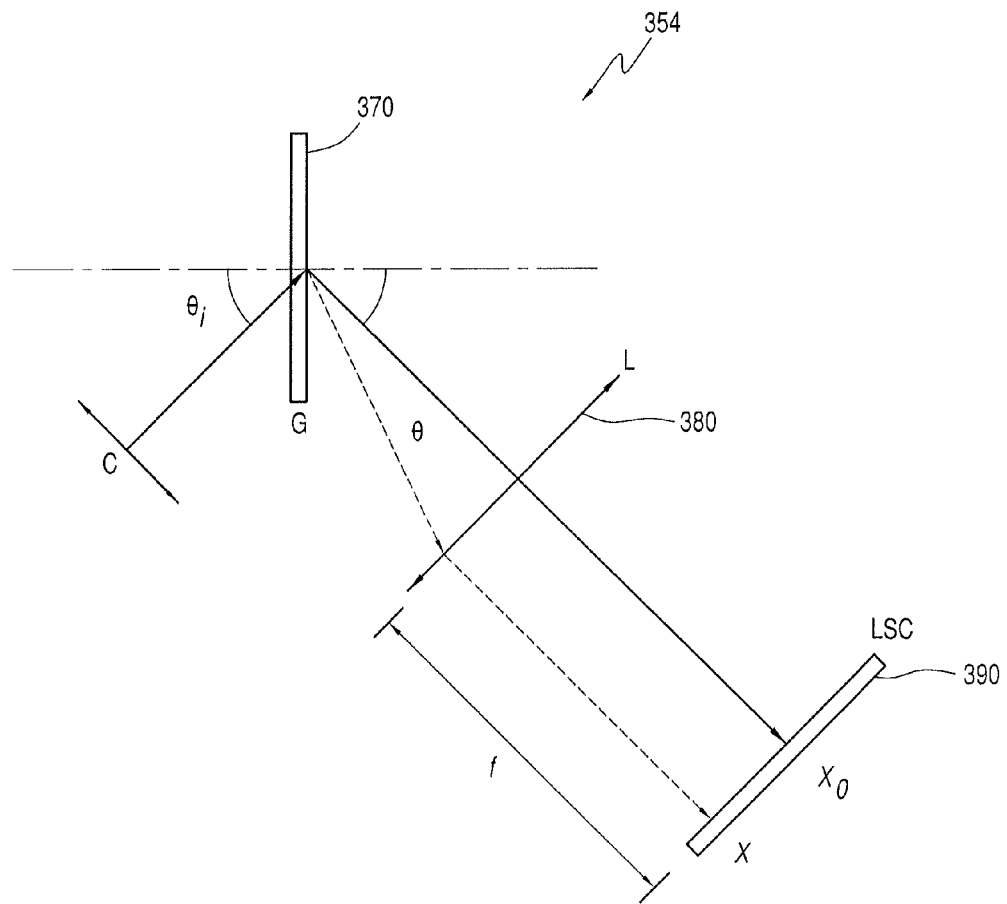
FIG. 3 is a schematic diagram of the imaging spectrometer used in the detection arm of the OCT system.

Referring to FIG. 3 showing a schematic of the spectrometer 354, the light emitting from optical fiber 350 consists of the individual wavelength components $\lambda$ of light source 310 and is incident on the transmission grating 370 at an angle $\theta_i$ and is dispersed at an angle equal to $\theta_i+\theta$. The angle $\theta_i$ is calculated using the grating equation (Eq. 2):

$$\lambda = d\sin(\theta_i) + d\sin(\theta_i+\theta), \quad \text{Eq. (2)}$$

where d is the grating period. Grating 370 is a transmission grating, such as a volume phase holographic (VPH) transmission grating with a spatial frequency of 1800 lines/mm, which is equal to a grating period of d=5.56×10−4 mm.

Solving Eq. (2) for the angle $\theta_i$ using the light source central wavelength $\lambda_0$=836 nm and setting the diffraction angle $\theta$=0:

$$\theta_i = \sin^{-1}\left(\frac{\lambda_0}{2d}\right) = 48.80° \quad \text{Eq. (3)}$$

According to the grating equation (Eq. 2), the dispersion angles for SLD light source 310 span from $\theta_1$=48.80°−5.07° to $\theta_2$=48.80°+5.65°.

As shown in the spectrometer schematic, the position x of a wavelength component on the sensor array is estimated from the following equation (Eq. 4):

$$x = f\tan\theta \quad \text{Eq. (4)}$$

where f is the focal length of imaging lens 380 of the spectrometer. The focal length of the lens is chosen to fill as many of the pixels on the sensor 390 as possible. Using a sensor array with N=4096 pixels and a pixel size of p=10 μm and an imaging lens with f=210 mm, the pixels on the sensor that are illuminated from the dispersed spectrum span from:

$$x_1 = f\tan(\theta_1-\theta_i) = -18.63 \text{ mm}$$

to $$x_2 = f\tan(\theta_2-\theta_i) = +20.78 \text{ mm}$$

and $x_0=0$ mm is the position of the central wavelength $\lambda_0=836$ nm. The spectral resolution can be approximately calculated using the following equation:

$$\delta\lambda \approx \frac{\Delta\lambda_{1\%}}{\frac{x_2-x}{p}} \quad \text{Eq. (5)}$$

Here, $$\frac{x_2-x}{p} = 3942$$

px is the number of pixels illuminated on the sensor by the spectrum at the 1% power level, giving an estimated spectral resolution of $\delta\lambda=0.017$ nm/px From the spectral resolution of the spectrometer, the estimated detectable free-space depth range is calculated using the following equation:

$$\Delta z = \frac{1}{4n}\frac{(\lambda_0)^2}{\delta\lambda} = 10.129 \text{ mm} \quad \text{Eq. (6)}$$

One requirement in order to achieve a high sensitivity OCT system is that the spectrometer must have high efficiency, i.e. optical losses in the device must be minimized. One method of reducing optical losses is by maximizing the coupling of the collected light to the individual camera pixels. This can be accomplished by ensuring that the focused beam spot size is smaller than size of a single pixel in detector 390, which is 10×10 µm, or is reduced as much as the optical assemblies allow.

Assuming a Gaussian beam profile, the beam waist diameter $2\omega$ at the focal plane of the imaging lens is given by the following equation:

$$2\omega = \frac{2\lambda f}{\pi\omega_0} \quad \text{Eq. (7)}$$

where f=210 mm is the focal length of the imaging lens and $\omega_0=14$ mm is the collimated beam diameter incident on the imaging lens. Using these example values for f and $\omega_0$, over the spectral band incident on the sensor from $\lambda_1=820$ nm to $\lambda_2=870$ nm, the calculated beam waist at the focal plane of the imaging lens varies from 15.12 µm (802 nm) to 16.62 µm (870 nm).

In one embodiment the sensor used is a line scan camera which detects the spectral interferogram, and it has a linear array of N=4096 pixels. The individual pixel locations are mapped to their corresponding wavelength of the detected spectral interferogram, which is determined primarily through the grating equation (Eq. 2). The distribution of wavelengths over the array is non-linear, so a calibration is performed to accurately map the pixel number to its corresponding wavelength. An imprecise spectrometer calibration may lead to errors when converting the spectral data to the depth-dependent reflectivity profiles that are used to construct a cross-sectional image, resulting in poor image quality. The non-linear distribution is approximated with a fourth-order polynomial, which maps the wavelength to the pixel location across the array:

$$\lambda = a_0 + a_1 x^1 + a_2 x^2 + a_3 x^3 + a_4 x^4 \quad \text{Eq. (8)}$$

where $a_0, a_1, a_2, a_3, a_4$ are the polynomial coefficients.

Calibration of the spectrometer is performed with a gas discharge spectral calibration Neon lamp. The Neon lamp emits multiple spectral lines at known wavelengths over the spectral range of the spectrometer. A multimode optical fiber cable (50 µm core) couples the light output from the Neon lamp to the spectrometer. The spectral lines are dispersed across the detector array and the exposure time of the camera is adjusted so that the low intensity light emitting from the calibration source can be detected. Several spectral lines of known wavelength are selected from the recorded spectrum, for example 8 spectral lines ($\lambda_0 \ldots \lambda_N$, N<8) may be used. Their corresponding pixel positions $x_0 \ldots x_N$, N<8 are recorded and a plot of the wavelength as a function of pixel number is obtained, which is used to calculate the polynomial coefficients $a_0, a_1, a_2, a_3, a_4$ from Eq. (8). Any suitable number of spectral lines may be used, for example N<3. Using more spectral lines may improve the accuracy of the calibration, for example using N=15 or N<15.

Other models of the non-linear distribution of wavelengths over the array may be used, including for example higher order polynomials.

An "A-scan" is a map of the reflectivity of the sample versus depth and is provided by the envelope of the measured interferogram pattern. A "B-scan" is a two-dimensional map of reflectivity versus depth and lateral extent that is built up using multiple A-scans that are acquired when a sample beam is scanned across the tissue surface.

Figure 4:
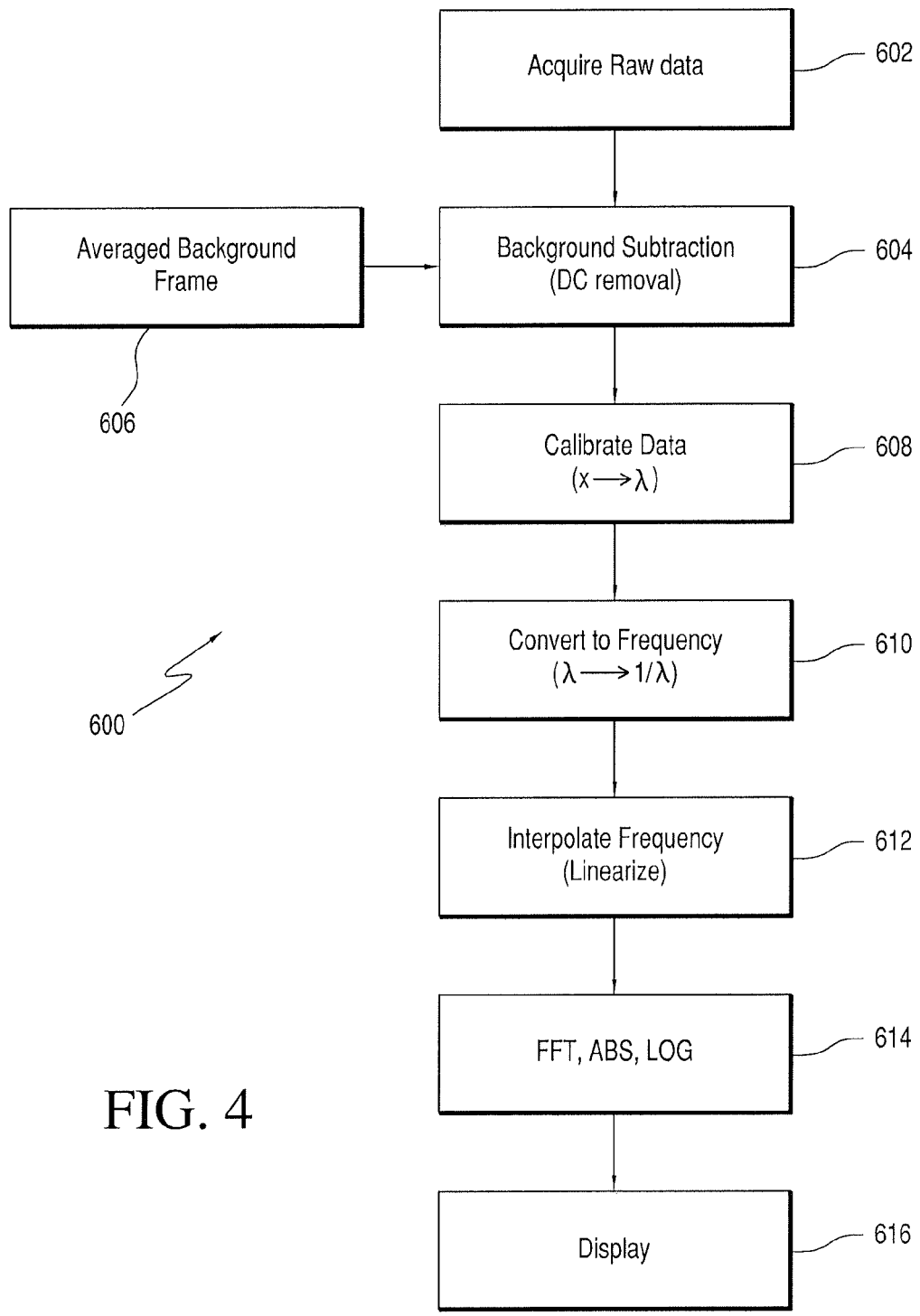
FIG. 4 is a schematic diagram of a signal processing algorithm used to process recorded interference data and convert the data to the depth dependent intensity profiles, or A-scans.

Referring to FIG. 4, the flowchart describes one embodiment of the present invention, a process 600 to convert raw image data acquired from the sensor (detector 390 in FIG. 2) to a depth-dependent reflectivity profile, or A-scan.

Raw image data is acquired at step 602. Spectral domain OCT systems typically suffer from several signal and noise sources that manifest as artifacts in the processed B-scan. Two common sources are the autocorrelation artifacts, which is the DC component of the spectral interferogram, and the so-called fixed pattern noise, which is typical of CMOS sensors in the detector. Both of these sources are corrected by performing a background subtraction as the first step in the signal processing pipeline. This is done by capturing the first B-scan in an acquisition sequence, which typically has 1000 A-lines, and averaging all of the A-lines in the B-scan. This results in a 1-D array of values 606 that contain the autocorrelation (DC signal) and fixed-pattern noise components. This array 606 is subtracted from each subsequent A-line acquired at step 604. Next, at step 608, the pixel data is converted from pixel number to wavelength by applying the calibration curve from Eq. (8).

Since the spectral interferogram must be Fourier transformed to frequency space in order to calculate the depth-dependent intensity, the wavelength data is converted to frequency at step 610 by taking the inverse:

$$f = \frac{1}{\lambda}.$$

After taking the inverse, the frequency array has generally a non-linear interval, so it is resampled to linearize the frequency data at step 612. The frequency interval is calculated based on the spectral span of the detector and the number of elements in the array, and the new frequency spectrum is interpolated with a cubic spline algorithm, resulting in an array of elements that contains the spectral interferogram that is linear in frequency.

Once the frequency data has been scaled and linearized, the following signal processing is performed at step 614:
- the intensity profile is obtained by a Fast-Fourier Transform (FFT);
- the absolute value of the complex result of the FFT is taken to return the magnitude of the signal;
- the log of the signal is taken to compress its dynamic range, resulting in a depth-dependent intensity profile (A-scan).

This type of signal processing contributes to providing a usable A-scan quickly so that an image can be provided to the output of the system (e.g. in the ocular of the operation microscope) in substantially real-time. Other types and combinations of signal processing may also be used to provide usable A-scans as will be understood by a person skilled in the art. The A-scan is displayed at step 616.

A cross-sectional image of the sample is generated by OCT system 300 by recording a series of adjacent depth scans (A-scans) that are scanned across the sample by transverse scanning unit 200. At each lateral position of the OCT beam, one line of data is read from linear array detector 390 and processed by computer 500, described above, to create one depth-dependent intensity profile of the backscattered signal (A-scan). A series of A-scans are recorded while transverse scanning unit scans the OCT beam across the sample in one cross-sectional plane (x-direction). Optical scanners 230 and 240 are driven by linear ramp signals to ensure the lateral scan velocity of the beam is constant. Additionally, objective lens 110 is positioned so that its back focal plane is located at the midpoint of optical scanners 230 and 240. This configuration assures that the chief rays of the OCT beam remain substantially parallel to the optical axis of surgical microscope 100, and normal to the sample or patient's eye 900. Normally incident rays are important to reduce image distortions due to refraction at individual surfaces.

The recorded series of adjacent A-scans, typically 100-1000, are then combined in computer 500 to create a 2-dimensional map of the backscattered intensity (B-scan), thereby revealing the internal structures of the patient's eye. The lateral length of the scan is limited by the aperture of objective lens 110, but can be large enough to cover the entire lateral dimension of a patient's eye.

As is shown in FIG. 2, OCT system 300 uses optical fiber 340 to direct its output to reference arm switch 400. Lens 410 collimates the output of the fiber and directs it through optical wedges 420 and 430. Optical wedge 420 is mounted in a fixed position and optical wedge 430 is mounted on a stage that translates the element laterally with respect to the optical beam, which is used to compensate for dispersion mismatch in the two arms of the interferometer, described below. The reference arm optical switch 400 comprises a pivoting mirror mounted on optical scanner 440, typically a galvanometer motor whose position is computer controlled. In its nominal state optical scanner 440 deflects the reference arm beam toward a retro-reflector comprising focusing lens 450 and fixed mirror 460. The optical path length between optical element 410 and 460 determines the zero-delay location, which corresponds to the location in the sample where interference can be detected. The zero-delay location determines the initial location of a single depth scan from the OCT system.

By applying a fixed voltage to optical scanner 440, the mirror pivots and directs the reference arm beam to lens 470, which focuses the beam on fixed mirror 480. The optical path length between elements 410 and 480 is chosen to be longer than the optical path length between elements 410 and 460 by an amount that is determined by the desired overlap of the top and bottom imaging windows, described below. Switching optical scanner 440 between the two optical paths 410 to 460 and 410 to 480 permits two distinct zero-delay locations to be scanned in rapid succession.

Other embodiments of the reference arm optical switch can be implemented by, for example, incorporating more than two optical paths to increase the scan depth further. A galvanometer-mounted mirror is the preferred embodiment for the reference arm switch due to its simple operation and fast response time, however other implementations of the optical switch are possible, including micro-electromechanical (MEMs) mirrors, integrated optical devices, and fiber-optic switches, all of which are capable of performing a similar function as will be understood by those skilled in the art.

As described herein, the reference arm optical switch is used generally for extending the imaging depth range in an OCT system.

Figure 5:
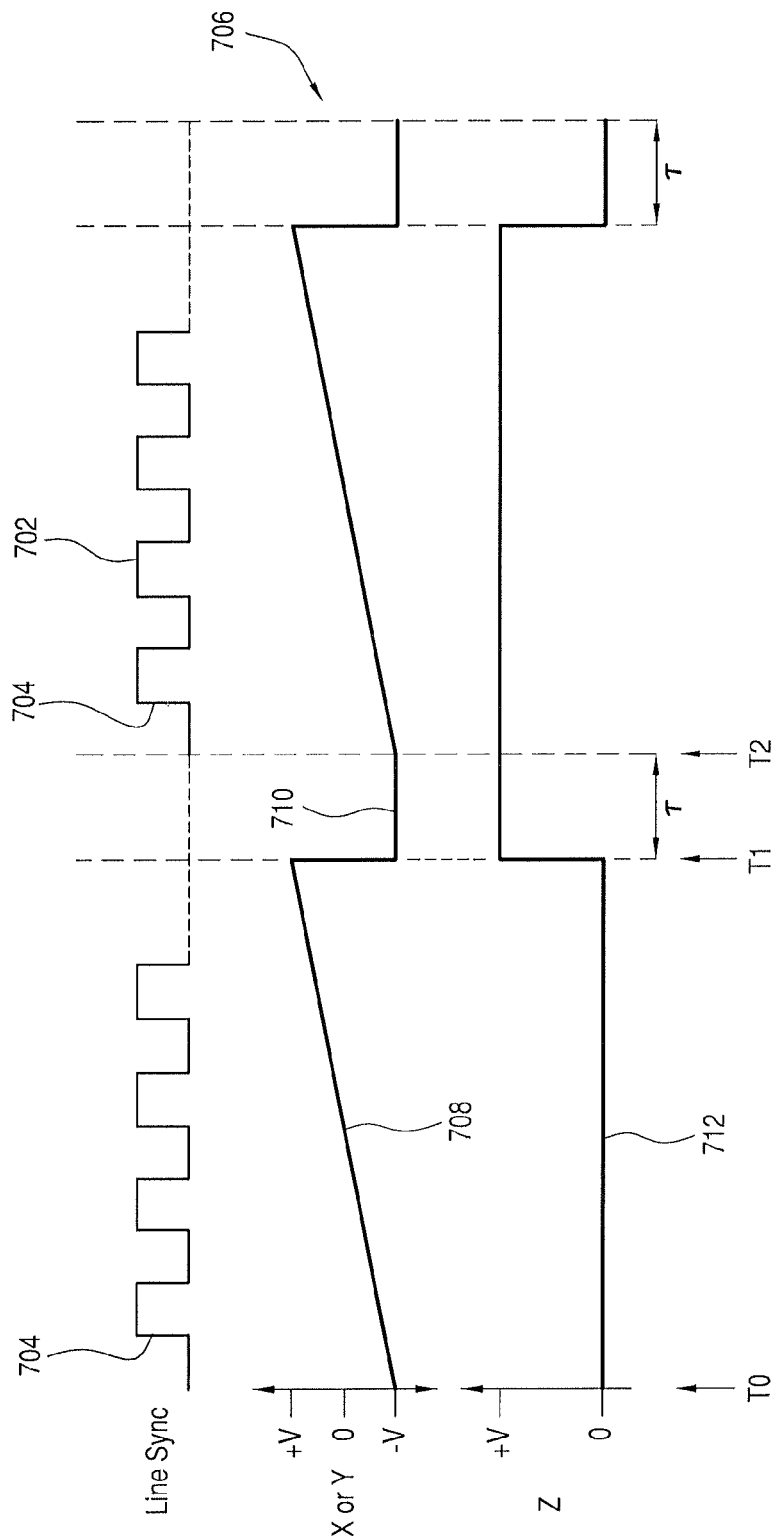
FIG. 5 is a timing diagram showing operation of an optical switch of the apparatus shown in FIG. 2.

FIG. 5 shows a timing diagram of the operation of the fast optical switch when implemented in the reference arm of a SD-OCT system. The top trace 702 is the line sync signal, which is used to control the exposure of the line-scan camera and synchronize the other control signals in the OCT system. The line sync can be generated either internally by the camera, or externally and supplied to the camera. Each rising edge 704 of the line sync triggers one acquisition of a spectrum from the camera, which corresponds to one A-line of data. This signal is repeated until the required number of A-lines have been recorded to construct one B-scan.

During the acquisition of one B-scan, the transverse scanners (optical scanners 230, 240 in FIG. 1), X or Y or both, are driven with a drive waveform to laterally scan the beam in the desired pattern. For a cross-sectional image in a single meridian, it is sufficient to drive either the X or Y scanners with a linear ramp function 706, from −V to +V so the beam scans across the sample at a constant velocity. At the completion of the first ramp 708 (X or Y) the scanner returns to its starting location −V 710.

During the first cycle, the Z scanner, which controls the optical switch 400, is held constant at its starting location 712, corresponding to the initial zero-delay location. At time T1, the transverse scanner (X or Y) returns to its initial location and the fast optical switch scanner (Z) is activated, deflecting the reference arm beam to a longer optical path, thereby shifting the zero-delay location to a new depth in the sample.

There is a delay τ0 between the time the optical switch 400 is activated and the time that it settles at its new location. This delay is on the order of 100-200 μs, which includes the settling time of the galvanometer and the time it takes the scanner to traverse the necessary angle. At time T2, the zero-delay has been shifted to its new location, and the acquisition of the second B-scan commences. The X or Y transverse scan pattern is repeated during the acquisition of the second B-scan, ensuring that the two frames are scanned in the same plane parallel to the optical axis. The two B-scans that have been recorded are then stitched together in a manner described below. By alternating the acquisition between a top and bottom frame, the amount of time in shifting the zero-delay location is minimized, thereby maximizing the total acquisition speed and reducing possible motion artifacts.

In other embodiments, the transverse scanners, X or Y or both do not return to the start configuration when the fast optical switch scanner (Z) is activated. For example, referring to FIG. 5, at time T1 the transverse scanner control would remain at +V while the scanner control changes from 0 to +V and after the delay τ the transverse scanner control would ramp down to −V.

Dispersion imbalance between the sample and reference arms (202, 342) of the interferometer degrades the axial resolution in OCT by broadening the signal peaks that are generated from reflections in the sample. First-order dispersion, or group-delay dispersion (GDD) is the result of a difference in the amount of dispersive optics in the sample and reference arm. Referring to FIG. 2, optical wedges 420 and 430 are used to compensate for the additional dispersion present in the sample arm 202 of the OCT system, which can be due to, for example, differences in fiber-optic lead lengths, or the dispersion of surgical microscope objective 110. By translating optical wedge 430 laterally with respect to the optical axis, a variable amount of glass in the optical path can be introduced, thereby adding the additional dispersion required. The opposing configuration of the wedges assures that the beam remains collinear and does not deviate from its optical axis while wedge 430 is translated to adjust the dispersion compensation.

The amount of dispersion compensation required is determined empirically, by minimizing the FWHM of the point spread function from a first-surface reflection in the sample arm as a function of the offset of optical wedge 430. Balancing the amount of dispersion in the sample and reference arms of the OCT system will optimize the axial resolution of the system at only one sample depth, the zero-delay location.

If the sample is a dispersive medium, like the human eye, then a second-order dispersion, or group-velocity dispersion (GVD), introduces a depth-dependent reduction in the axial resolution. GVD can be compensated using numerical techniques, such as those described in U.S. Pat. No. 7,719,692 B2, hereby incorporated by reference herein, as if made a part of this specification, where the GVD is automatically removed from the spectral interferogram during signal processing.

One feature of GVD is that its impact on degrading image quality increases with increasing source bandwidth. By limiting the source bandwidth to approximately 70 nm or less, the depth-dependent loss of axial resolution is kept within acceptable limits. Furthermore, when imaging the anterior segment of the human eye, the length of dispersive medium is limited to approximately 10-12 mm, which in turn, limits the impact of GVD. This is in contrast to retinal imaging, where the probe beam must pass through the full axial length of the eye (approximately 24-25 mm), which has a much more significant impact on the imaging resolution.

The depth range of conventional SD-OCT is limited by the spectral resolution of the spectrometer in the detection arm. Reflections from longer axial lengths are encoded as higher fringe frequencies in the spectral interferogram. As the fringe frequency increases beyond the spatial dimension of the individual pixels in the detector array, the spectral interferogram becomes under-sampled according to the Nyquist criterion, which leads to the theoretical depth range limit in Eq. (1).

Figure 6:
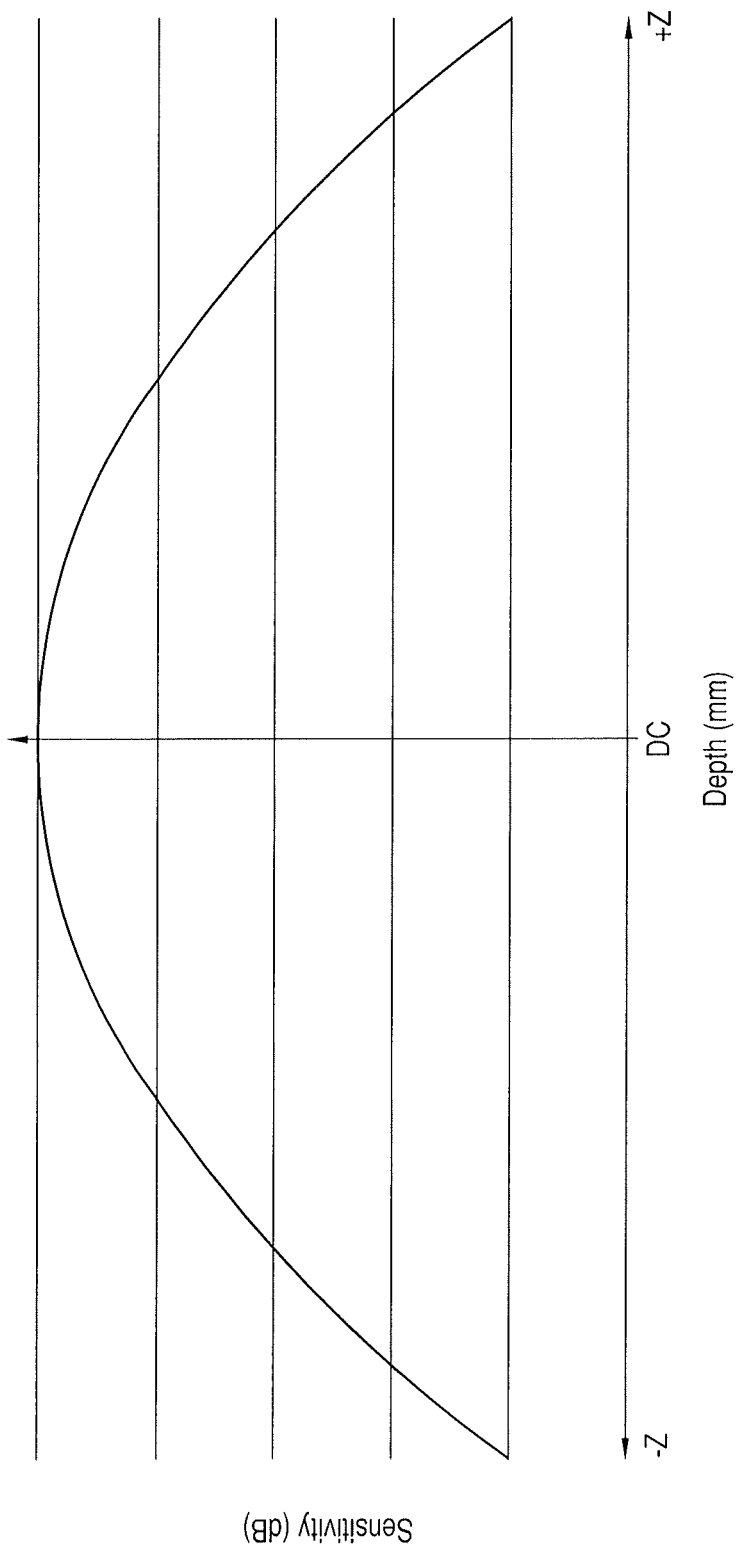
FIG. 6 shows a plot of sensitivity against frequency about a zero-delay location for an OCT system.

FIG. 6 shows an example plot of sensitivity against frequency about a zero-delay location for an OCT system showing the fall off in sensitivity at longer axial lengths, the scan ranging from position (DC−Z) to position (DC+Z).

In practice, several factors contribute to the depth range limit, which lead to a depth dependent falloff in the sensitivity profile. That is, the interference signal is stronger at the zero-delay location than it is at the deepest part of its range. This reduces the useable depth range for imaging by as much as one-half.

For typical retinal imaging where only about 2 mm of imaging range are required, this does not pose a serious problem. However, for anterior segment imaging where >10 mm of range is required, this imposes limitations on the system performance due to the design trade-offs of the spectrometer. For a linear array sensor with a finite number of pixels, increasing the spectral resolution of the spectrometer reduces the light source spectral span on the array, thereby reducing the source bandwidth, and reducing the axial resolution of the OCT system. For a given required axial resolution, the imaging depth may be increased by employing a linear array sensor with a larger number of pixels. However, this increases cost and complexity. Alternatively, a method to capture multiple frames in rapid succession, as described herein, can be used.

Figure 7:
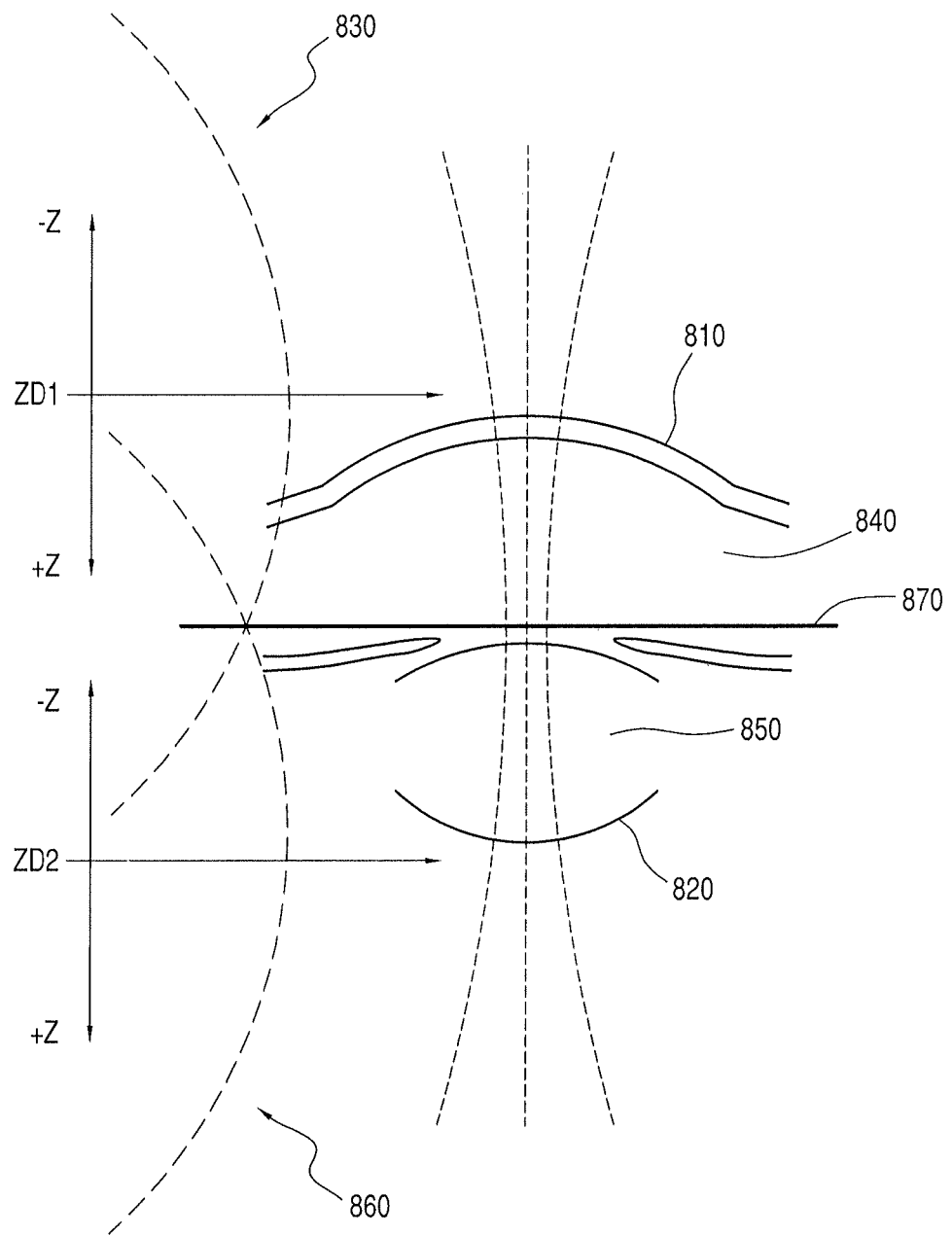
FIG. 7 shows a representation of an anterior segment of an eye and a location of two zero-delay locations provided by an optical switch of the apparatus shown in FIG. 2.

For imaging the entire anterior segment of the eye, the imaging depth in tissue may be extended beyond approximately 10 mm by employing the reference arm optical switch described above. Referring to FIGS. 2 and 7, a method to use both the positive and negative sides of the complex scan with the reference arm optical switch is described.

FIG. 7 shows a representation of an anterior segment of an eye and a location of two zero-delay locations provided by the optical switch 400. Reference arm mirror 460 is positioned such that its zero-delay location (ZD1) is slightly anterior to the cornea surface 810, as in FIG. 7. Reference arm mirror 480 is positioned such that its zero-delay location (ZD2) is slightly posterior to the posterior crystalline lens surface 820, as in FIG. 7. The first frame recorded 830 consists of the cornea down to through the anterior chamber 840, which is captured on the positive side of the top half-scan.

When the reference arm optical switch 400 is activated, the zero-delay location shifts to ZD2, and the second frame 860 captures the crystalline lens 850, which is recorded on the negative side of the bottom half-scan. After the two frames are captured, they are combined in the computer 150 by cropping the low-sensitivity end of each scan and creating a new image, where the two half-frames are joined together at the crop line 870. In some embodiments the cropping results in a switch from one half-frame to another half-frame at the crop line. In other embodiments, the two half-frames may be combined, for example by averaging the image in a region before switching to use of only one of the half-frames, or using another method of transitioning between the half frames. Where the zero-delay locations and the imaging depth are such that there is no or substantially no overlap between the imaging depths, then the cropping may be omitted.

Figure 8:
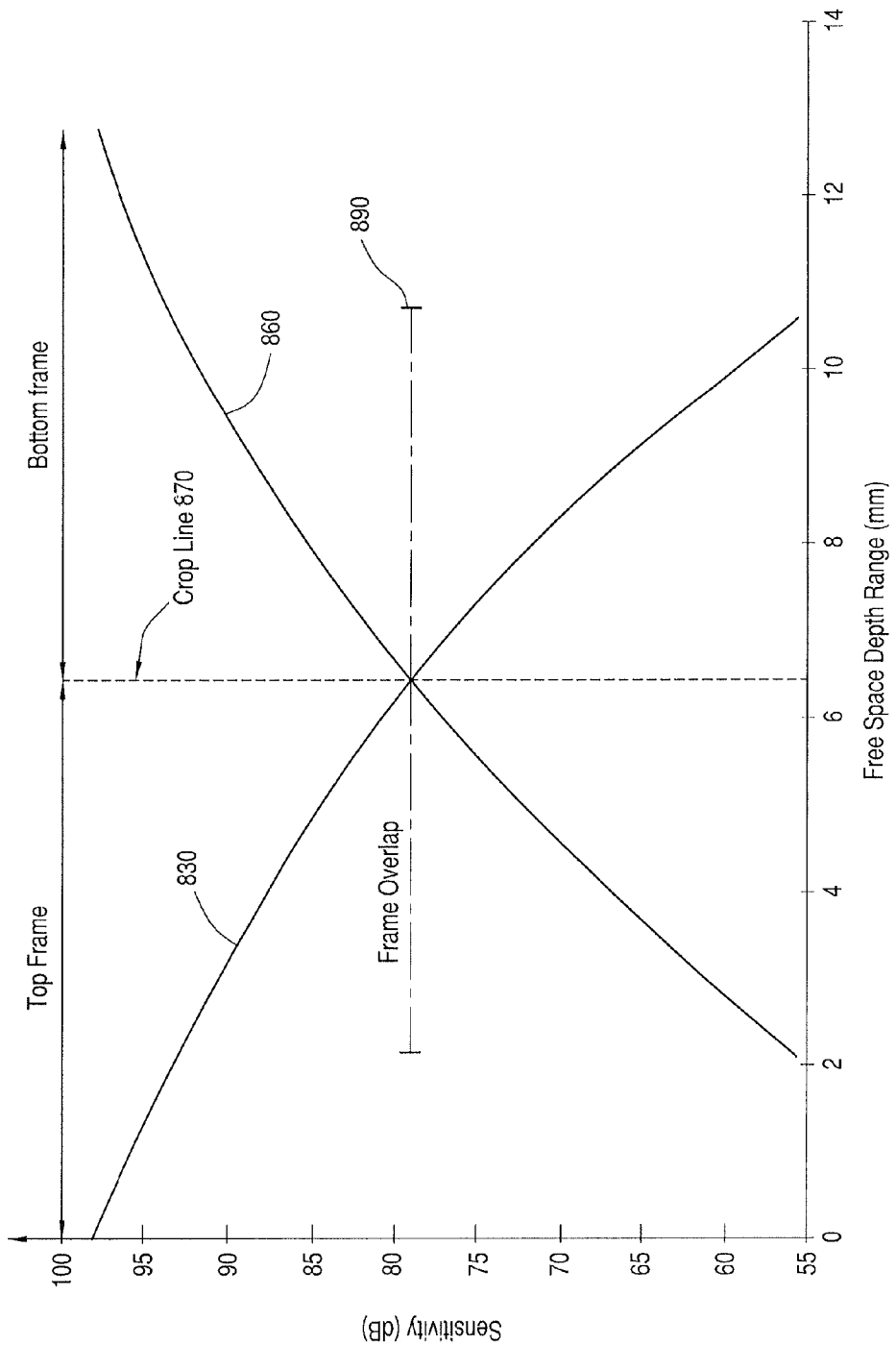
FIG. 8 shows a representation of two individual images from the extended depth spectrometer of FIG. 2, overlapped and summed to produce the single image with increased imaging depth and with improved sensitivity roll-off performance.
Figure 9:
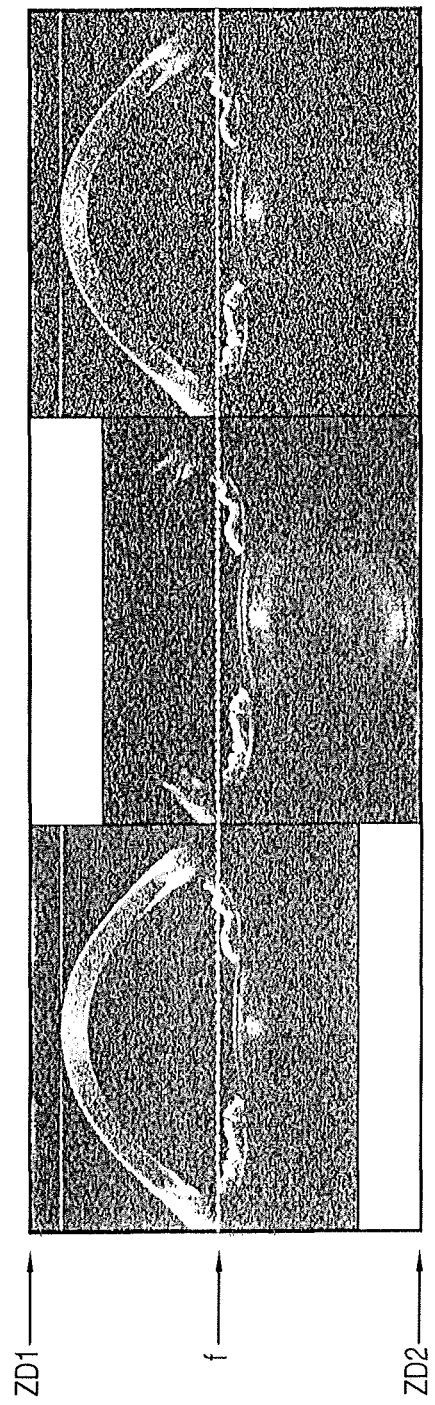
FIG. 9 shows example images captured at two zero-delay locations and a composite image formed from the two images.

FIG. 8 shows a representation of the two individual images from first frame 830 and second frame 860, overlapped and summed to produce a single image with increased imaging depth and with improved sensitivity roll-off performance. The amount of distance that the two images overlap 890 is adjustable using software processing methods and is chosen based on image quality.

A normal calibrated free-space depth range of approximately 10.6 mm can be achieved with the spectrometer described herein. By applying the reference arm optical switch, the free-space depth range can be extended to at least 12.7 mm, which is sufficient to image substantially the entire anterior segment of a human eye, from anterior cornea surface to the posterior crystalline lens surface, with increased sensitivity. Note that any technical improvements to the sensitivity falloff will immediately extend the imaging range further by reducing the frame overlap that is required to construct the final B-scan. Because the high-sensitivity end of each frame is used to create the image, the deleterious effects of the sensitivity falloff inherent in FD-OCT are reduced.

In some embodiments, all the image data can be measured from a first switch position to form a first composite image. This is followed by measuring all the image data from a second switch position to form a second composite image. The two composite images are then stitched together to form a final composite image. For example, all the A-scans are taken from the first switch position to form a first B-scan. This is followed by taking all the A-scans from the second switch position to form a second B-scan. Following this, the two B-scans are stitched together.

In other embodiments, image data (e.g. a first A-scan) is acquired from the first switch position, followed by acquiring further image data (e.g. a second A-scan) from the second switch position. These two are then stitched together. This can be repeated until multiple stitched data pairs have been acquired, and these can then be combined into a single stitched composite image.

Another limitation in known FD-OCT, both for SS-OCT and SD-OCT, is the so-called complex conjugate artifact, which arises as a result of the symmetry properties of the Fourier Transform of real signals, which produces identical signal peaks at both positive and negative frequencies. The complex conjugate artefact is manifested as a mirror image of the sample being scanned. Methods exist for removing the complex conjugate artifacts and using the full range of the complex spectrum and are described in, for example U.S. Pat. App. Pub. US 2011/0102802 A1. However, they generally suffer from reduced imaging speeds, as multiple frames of data (3-5) are required to construct a single B-scan and additional signal processing is required to eliminate the mirror image after the multiple acquisitions have been completed. The optical switching method described herein can create an entire B-scan from just 2 frames of data in real time and there is very little imaging time lost during the switching process. In addition, no additional signal processing steps are required.

During regular ophthalmic OCT scanning, the zero-delay location is positioned such that the structure of interest is completely located on one half side of the imaging frame, either the positive frequency (+Z) or negative frequency (−Z) side.

For typical retinal imaging, this poses no problem since the zero-delay location will be positioned slightly anterior to the retinal boundary, so that the negative frequency side (−Z) of the scan is completely located in the vitreous, where there are no significant structures to generate mirror-image artifacts. For typical corneal imaging, this is also not a problem for the same reason, since the negative frequency side of the scan is located outside the eye in air, where no mirror-image artifacts can be seen.

However, for crystalline lens imaging in the eye, this is problematic since if one were to position the zero-delay location near the anterior surface of the crystalline lens, a mirror-image artifact would be created from the reflections of the cornea, which would be superimposed on the image of the crystalline lens. In order to image the crystalline lens without mirror-image artifacts, the zero-delay location is located near the posterior lens boundary, such that the back-half, or negative frequency side of the scan is used for imaging. In this situation, the front-half, or positive frequency side of the scan is located in the vitreous where no significant structures can generate artifacts. This method of imaging the crystalline lens in real time is feasible with only the spectrometer described in this invention because it is possible to have an imaging depth in tissue of approximately 7.6 mm or more.

Therefore, in the system described herein no mirror-image artifacts are created since the complex conjugate of the scan is always located in a region without significant structure. For the top frame including the cornea, the negative side of the scan is located outside the eye, where the air medium will not create artifacts. For the bottom frame including the crystalline lens, the positive side of the scan is located in the vitreous, where normally there is no significant structure to generate artifacts.

Referring to FIG. 1, the focal length of objective 110 is chosen to provide sufficient depth of focus to image the eye within the complete scan depth range of the OCT system. The depth of focus of the scan is closely matched to the required scan depth. Known OCT systems use objective lenses that produce a small probe beam focal spot size. Typically, for limited range depth scanning of 2-3 mm, a short depth of focus with small focal spot size is desired to maximize the lateral resolution of the image. As described herein, however, a long depth of focus of approximately 5-10 mm is used to image substantially the entire crystalline lens during surgery. For extended depth imaging, a longer depth of focus in the order of the total scan depth range is required to ensure that the reflected signal strength is sufficient to maintain good image contrast throughout the scan range.

For anterior segment imaging with a required 12 mm free-space scan depth, the depth of focus, or confocal parameter, defined as twice the Rayleigh range ($z_r$) for a Gaussian beam is approximately 12 mm as well. To achieve this depth of focus at NIR wavelengths near 830 nm, the f-number (f/#=f/D) for a given objective focal length (f) and beam diameter (D) is:

$$F/\# = \sqrt{\frac{\pi}{4\lambda}} z_r \approx 75 \qquad \text{Eq. (9)}$$

The location of the focal plane in the eye with respect to both of the zero-delay locations impacts on the reference arm optical switching method because both the top frame image and bottom frame image are preferably nearly in focus at all times. The focal plane is ideally located in a plane that corresponds approximately to the mid-point of the two zero-delay locations. For whole anterior segment imaging, this location is in the anterior chamber of the eye, close to the anterior surface of the crystalline lens. By locating a single beam focus with relatively long depth of focus, this eliminates the need for so-called dynamic focusing methods where multiple focal planes are scanned in succession and synchronized with the acquisition of the individual frames from the OCT system. Such methods have been described in U.S. Patent Application Publication US 2011/0102802 A1 in the application of switching scanning modes from a telecentric anterior segment scan to a retinal imaging scan with iris pivot. While dynamic focusing methods may improve the image quality for extended depth OCT, they require the physical movement of optical components in the delivery path, which typically have large inertia, and will generally have very slow response times, precluding them from high-speed imaging. The single, long depth of focus method described above allows the two frames acquired using the reference arm optical switch to be acquired at high-speed, without any additional delay between frames.

The method and system as described above can also be implemented using a swept-source (SS)-OCT instead of a spectral-domain (SD)-OCT. In such an embodiment, the nominal scan depth range of the SS-OCT system can be extended by the reference arm switch in a manner similar to that depicted in the timing diagram of FIG. 5, where the rising edge (704) of the line sync signal corresponds to the acquisition of one A-scan and the reference arm switch (712) is operated in the same manner as that described above for a SD-OCT system.

While the present invention has been described in detail with reference to specific embodiments thereof, it will be apparent to one skilled in the field that various changes, modifications and substitutions can be made, and equivalents employed without departing from, and are intended to be included within, the scope of the claims presented herein, as well as the claims presented in any subsequent US Utility Application based upon, and claiming priority from, the present US Provisional Application.

It will be understood that the invention disclosed and defined in this specification extends to all alternative combinations of two or more of the individual features mentioned or evident from the text or drawings. All of these different combinations constitute various alternative aspects of the invention.

The invention claimed is:

1. An intraocular imaging method comprising:
    receiving, with an optical coherence tomography system, image information of an ocular system at a first image depth range and a second image depth range, the second image depth range overlapping the first image depth range across an overlap region, the image information at each said depth comprising a positive and a negative frequency side about a zero delay location, wherein the overlap region comprises the positive frequency side of the image information of one said image depth range and the negative frequency side of the image information of the other said image depth range;
    forming first image data from the image information, the first image data relating to a first image at the first image depth range;
    forming second image data from the image information, the second image data relating to a second image at the second image depth range;
    cropping said first and second images at a location in the overlap region;
    producing a composite image by combining the cropped first and second images.

2. The method of claim 1 wherein the first image data comprises one or more first A-scans, the second image data comprises one or more second A-scans, and wherein the method further comprises:
    forming a first B-scan comprising said first A-scans;
    forming a second B-scan comprising said second A-scans;
    wherein said producing a composite image comprises combining the first B-scan and the second B-scan.

3. The method of claim 2 further comprising:
    forming one or more further B-scans, the one or more further B-scans comprising a plurality of A-scans at image depth ranges different from the first and second image depth ranges,
    wherein said producing a composite image comprises combining the first B-scan, the second B-scan and said one or more further B-scans.

4. The method of claim 1 wherein:
    said receiving comprises acquiring raw data; and
    said forming comprises removing artifacts from the raw data by performing a background subtraction to provide cleaned raw data.

5. The method of claim 4, wherein said first image data and said second image data both comprise an array of values and wherein performing the background subtraction comprises subtracting an array of values representing autocorrelation artifacts and fixed pattern noise.

6. The method of claim 5, further comprising, before said background subtraction, forming said array of values representing autocorrelation artifacts and fixed pattern noise by averaging image data comprising a plurality of A-scans.

7. The method of claim 4, wherein said receiving comprises receiving wavelength data and said forming further comprises:
    converting the wavelength data into non-linear frequency domain data;
    resampling the frequency array to provide linearized data; and
    processing the linearized data to provide the image data.

8. The method of claim 7 wherein said processing comprises:
    performing a Fourier transform on the linearized data to provide an intensity profile and a complex result;
    determining an absolute value of the complex result to provide magnitude data; and
    determining a logarithm of the magnitude data to provide a compressed dynamic range.

9. The method of claim 1 wherein the location of the first image depth range is selected so that the image information at the first image depth range includes substantially no mirror-image artifacts and the location of the second image depth range is selected so that the second imaging frame includes substantially no mirror-image artifacts.

10. The method of claim 1, wherein the ocular system comprises a cornea and a crystalline lens, wherein,
    the first image depth range is selected so that the zero delay location is one of anterior to the cornea and posterior to the crystalline lens, and
    the second image depth range is selected so that the zero delay location is posterior to the crystalline lens or anterior to the cornea respectively.

11. The method of claim 1, wherein said optical coherence tomography system includes an objective lens and wherein the objective lens is configured to provide a focal plane at a mid-point between the zero delay location at the first image depth range and the zero delay location at the second image depth range.

12. The method of claim 11, wherein said optical coherence tomography system includes a first and a second lateral scanner and is configured to have a back focal plane located between the first and the second lateral scanner.

13. The method of claim 11, wherein said cropping is performed at or near a location corresponding to the location of said focal plane.

14. The method of claim 1 further comprising the step of:
    providing the composite image to an operation microscope.

15. An intraocular imaging system comprising:
    a spectrometer;
    an interferometer comprising a sample arm and a reference arm, and
    an image processor;
    wherein the interferometer is configured to comprise a plurality of optical paths of different path lengths along the reference arm and to switch between the optical paths, the optical paths causing the imaging system to image at different imaging ranges comprising an overlap region comprising the positive frequency side of the image information of one said image depth range and the negative frequency side of the image information of the other said image depth range;
    wherein the intraocular system is arranged to operate said spectrometer and interferometer to provide the image processor image data over said imaging ranges and wherein the image processor is arranged to combine the image data to form a composite image extending over an imaging range longer than the imaging ranges formed by the individual path lengths.

16. The intraocular imaging system of claim 15, comprising an objective lens configured to provide a focal plane at a location in the overlap region.

17. The intraocular imaging system of claim 16, comprising a first lateral scanner and a second lateral scanner for controlling a position of said imaging range, wherein the intraocular imaging system is configured to have a back focal plane located between the first and the second lateral scanners.

18. The intraocular imaging system of claim 16, wherein the image processor is arranged to form B-scan data from said image data and crop the B-scan data at said path lengths at or around a location corresponding to the location of said focal plane.

19. The intraocular imaging system of claim 15, wherein the interferometer comprises a sensor comprising individual pixel locations, the image processor comprises a map of the individual pixel locations to a wavelength, the map configured to calibrate for non-linear distribution of the wavelengths across the pixel locations.

20. The intraocular imaging system of claim 19, wherein said map comprises a basis function in the form of a fourth-order polynomial and coefficients for the basis function.

21. An apparatus comprising the system of claim 15.

22. A method for imaging an eye comprising the steps of:
using an optical coherence tomography system forming image data of an image of the ocular system at a first image depth range and at a second image depth range, different from the first depth range, wherein at least one of the depth ranges is positioned so that the image at that depth range comprises substantially no structure in one of a positive frequency side and a negative frequency side; and
combining the image formed at the first image depth range and the second image depth range to form a composite image with a larger depth range than either of the first image depth range or the second image depth range alone.

23. The method of claim 22, wherein both of the depth ranges are positioned so that the image at that depth range comprises substantially no structure in one of a positive frequency side and a negative frequency side and wherein structure of the eye that is the subject of imaging is located in the positive frequency side the image at one said depth range and in the negative frequency side of the image at the other said depth range.

24. The method of claim 23, wherein said structure of the eye comprises the cornea and the crystalline lens.

* * * * *